United States Patent [19]

Spitzer

[11] 4,453,537

[45] Jun. 12, 1984

[54] APPARATUS FOR POWERING A BODY IMPLANT DEVICE

[76] Inventor: Daniel E. Spitzer, 435 E. 30 St., New York, N.Y. 10016

[21] Appl. No.: 290,105

[22] Filed: Aug. 4, 1981

[51] Int. Cl.³ .............................................. A61F 1/00
[52] U.S. Cl. ........................................ 128/1 D; 3/1.7
[58] Field of Search ............ 128/1 D, 419 B, 419 PS; 3/1.7

[56] References Cited

U.S. PATENT DOCUMENTS

| | | | |
|---|---|---|---|
| 3,563,245 | 2/1971 | McLean et al. | 128/419 PS |
| 3,693,625 | 9/1972 | Aupman | 128/419 B |
| 4,222,365 | 9/1980 | Backhouse | 128/419 PG |

Primary Examiner—William E. Kamm
Attorney, Agent, or Firm—Hubbell, Cohen, Stiefel & Gross

[57] ABSTRACT

An apparatus for powering a pressure actuated body implant device is disclosed. Preferably, the apparatus is utilized to power an artificial heart. The apparatus comprises a reservoir implantable in the body and attachable to a body muscle, a pacemaker having stimulatory electrodes for connection to the body muscle and sensor electrodes for sensing the physiological needs of the body and power output of the body muscle, and tubing for connecting the reservoir to the artificial heart. The apparatus is totally implantable with the body and is toally independent of any external power source.

20 Claims, 8 Drawing Figures

FIG. 7.
FIG. 8.
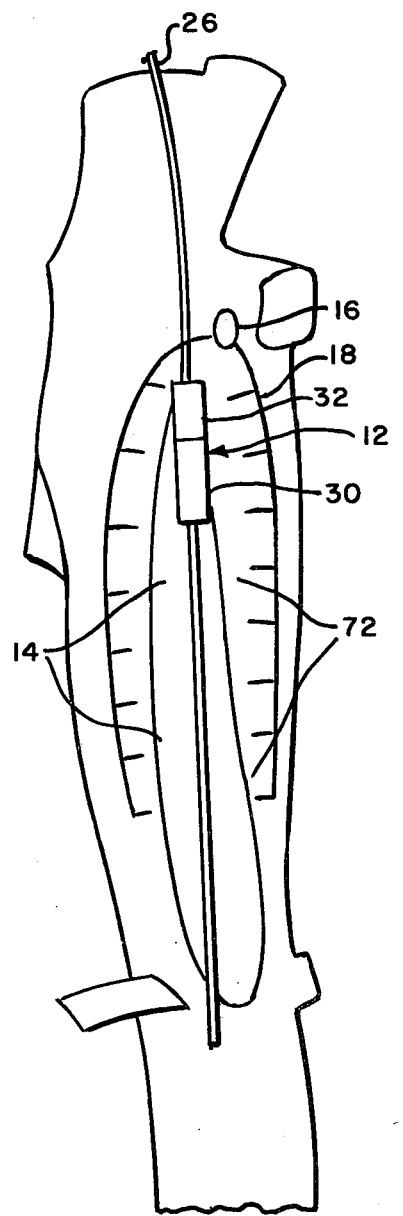
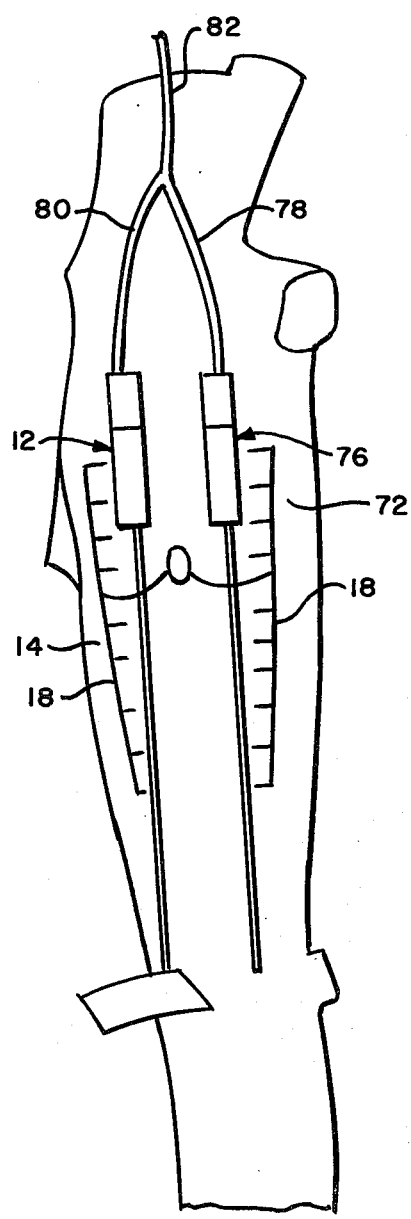

APPARATUS FOR POWERING A BODY IMPLANT DEVICE

TECHNICAL FIELD

This invention relates generally to an apparatus for powering a pressure actuated body implant device. In particular, the invention relates to an apparatus for powering a pressure actuated artificial heart. The apparatus is implantable within the body and acts in association with a body muscle to power an artificial heart without the need for an external power source.

BACKGROUND ART

Heart disease continues to take a heavy toll of human life. It is responsible for nearly a million deaths a year in the U.S. alone. The toll has been reduced to some extent by improved and new medical procedures, new drugs, pacemakers and most recently by the employment of ventricular assist devices. However, in many cases, replacement of the diseased heart with a healthy heart is the only manner of treating and curing the patient. One of the major problems with this method of treatment is that there are too few donors. For example, in 1978 only 31 people received transplanted hearts, whereas a panel of the National Heart, Lung and Blood Institute has estimated that from 17,000 to 50,000 people per year could use a transplanted heart.

A possible solution to this problem is a totally artificial heart. The development of such a device began in 1957. Since 1975 a number of artificial hearts have been developed and tested in animals. Unfortunately, most of the artificial hearts developed prior to 1970 were not successful for various reasons. In 1970 a series of developments made the prospect for the device look better. A major advance was the design of a heart whose pumping element was a diaphram. This principle was introduced by Clifford S. Kwan-Gett. Basically, the artificial heart developed by Kwan-Gett comprises a chamber containing a deformable diaphram. The heart was driven by an external pump which periodically pumps fluid into the heart chamber to deform the diaphram and thereby expel blood from the artificial heart chamber. Notwithstanding, the improved diaphram system, Kwan-Gett's artificial heart, along with other hearts of similar design and construction, did not prove to be as successful as had been hoped due to shape and size problems.

In 1972, the diaphram principle was used by Robert Jarvik to design a more anatomically acceptable artificial heart. In animal testing, the Jarvik artificial heart has been very successful. The most recent model, the Jarvik-7 heart which was developed in 1979 has been remarkably successful. The Jarvik-7 heart has been implanted in calves which subsequently have survived for considerable periods of time. Despite the success of the Jarvik heart, the system utilized to power the heart remains a major problem which has stymied the development of artificial hearts. The pneumatically powered artificial hearts, including the Jarvik-7 heart, that have proven successful in animals are not portable. The animal is confined to a cage, tethered to a large drive system and exercised only on a tread mill. Such conditions would be unacceptable for human beings. Even if compressed air devices were made portable, the large pneumatic tubes that enter the chest would be uncomfortable and would carry a high risk of infection at the point of entry.

Ventricular assist devices, which assist the natural heart by supplementing the function of the left ventricle have spurred the development of an improved power system. While not as large as artificial hearts, ventricular assist devices work on the same principle as the artificial heart. Thus, they too require a pneumatic or hydraulic power source. An example of one such ventricular assist device is disclosed in Runge U.S. Pat. No. 4,176,411. The device disclosed by Runge comprises a flexible dacron conduit disposed between the left atrium of the heart and the descending thoracic aorta and surrounded by an artificial muscle sheath. In operation, the artificial muscle sheath is electrically stimulated to contract against the flexible dacron conduit to force blood to flow from the left atrium in to the aorta, thus aiding corporeal circulation.

The most recent development in an improved power system is an electrohydraulic energy converter that is presently being design by Jarvik in collaboration with Milton Isaacson of New-Tech, Inc. This electrohydraulic energy converter has only one moving part. The impeller of an axial flow pump is attached to the rotor supported by a single hydrodynamic bearing. Reversing the rotation pump reverses the direction of the hydraulic flow. The hydraulic fluid (silicon oil of low viscosity) actuates the diaphram of a blood pump much as compressed air does. In a left ventricle cardiac assist device the axial flow pump moves the hydraulic fluid from a reservoir sack into the blood pump and back. In a total artificial heart the hydraulic fluid is pumped back and forth between the right and left ventricles. The energy converter is so small that it can be implanted without impinging on vital structures. The converter, however, requires an external battery and an electronics package which is connected to the heart by a small cable that passes through the chest. The batteries weigh from 2 to 5 lbs. and are worn in a vest or on a belt. It is necessary to replace the rechargable batteries once or twice a day. Although this device contains many of the desirable features of a portable artificial heart for human use, it nevertheless has many of the problems of the totally external pneumatic pumps. The electrohydraulic energy converter is not a completely internal power system, but rather is dependent upon an external power source. Also, like the external pneumatic pumps, this new device has wires that enter the chest which would result in a high risk of infection at the point of entry. Moreover, this new device is dependent on a battery system which must be continually recharged and which must be worn on a belt or vest.

The present invention solves the problems of the prior art pumping devices since it is directed to a totally internal system for powering artificial hearts, ventricular assist devices and the like.

The present invention was first disclosed to the U.S. Patent and Trademark Office in Disclosure Document 97,636 dated Feb. 10, 1981.

DISCLOSURE OF THE INVENTION

According to the present invention, I have developed an apparatus for powering a body implant device, such as a pressure actuated artificial heart, ventricular assist device, or artificial diaphram, which overcomes the disadvantages of the prior art.

In the preferred embodiment, the apparatus is utilized to power an artificial heart. The principal components of the apparatus include a piston-cylinder reservoir implantable in the body and attachable to a body muscle, a pacemaker having stimulatory electrodes for connection to the body muscle and sensor electrodes for sensing the physiological needs of the body and power output of the body muscle, and tubing for connecting the reservoir to the artificial heart. The apparatus is totally implantable within the body and is totally independent of any external power source.

The fluid containing reservoir which is implantable in the body and attachable to a body muscle comprises a piston slidably disposed within a cylinder. Preferably, the piston-cylinder reservoir is implanted in the thigh and attached to the rectus femoris muscle. Prior to implantation of the reservoir, the rectus femoris muscle is exposed and the sensory and motor innervation of the muscle are sacrificed by normal surgical procedures. In addition, the origin and insertion of the muscle are severed. The piston cylinder reservoir is then implanted in the thigh and the insertion end of the muscle is attached to the cylinder and the origin end of the muscle is attached to the piston.

The piston-cylinder reservoir is filled with a fluid such as a gas like nitrogen or a liquid such as silicon or oil, and connected to the artificial heart by a biocompatible flexible plastic tubing. Contraction of the rectus femoris muscle forces the piston into the cylinder thereby pressurizing the fluid contained within the cylinder and causing it to flow out of the cylinder and through the flexible plastic tubing toward the artificial heart.

A pacemaker is utilized periodically to stimulate the rectus femoris muscle, causing it to contract. Preferably, the pacemaker is implanted in the thigh near the piston-cylinder reservoir. The pacemaker includes stimulatory electrodes which are woven through the rectus femoris muscle. The pacemaker also includes sensory electrodes which sense the body's physiological needs and the power output of the rectus femoris muscle. If the atrial portion of the natural heart remains after implantation of the artificial heart, a sensor is implanted into the atria to sense the frequency of the endogenously controlled sinoatrial or atrioventricular (AV) node. The sinoatrial node initiates the cardiac cycle, and thereby sets the basic pace for the heart. Once an electrical pulse is initiated by the sinoatrial node, the impulse spreads out over the atria to the atrioventricular node. Thus, by sensing the frequency of the endogeniously controlled SA or AV node, the physiological needs of the body can be determined. The information obtained from the atrial sensor is continuously transmitted to a microprocessor which is contained in the pacemaker.

In addition to sensing the body's physiological needs by means of the atrial sensor, it is also necessary to continuously monitor the power being exerted by the rectus femoris muscle during contraction. The power produced by the muscle may be monitored by connecting a tension sensor to strain and position gauges mounted on the piston-cylinder reservoir. Such a sensor monitors the tension exerted by the muscle on the reservoir when the muscle is contracted. Preferably, a pressure sensor is positioned within the flexible tubing connecting the reservoir to the artificial heart for measuring the pressure exerted by the fluid as it is expelled from the reservoir. In this manner, this sensor can also monitor the power output of the muscle when the muscle contracts. Preferably both power sensors are used with the atrial sensor.

All the information obtained by the three sensors is continually transmitted to the microprocessor contained within the pacemaker. Based on the information transmitted to the microprocessor by the sensors, the appropriate electrical signals are transmitted by the pacemaker through the stimulatory electrodes to stimulate the rectus femoris muscle, resulting in generation of the appropriate fluid pressure in the reservoir and, thus, the appropriate cardiac output. The intensity, frequency and duration of the stimulation will, of course, vary depending upon the body's physiological needs.

If, however, the atrial portion of the natural heart does not remain after the implantation of an artificial heart, one or more other sensors may be used in place of the atrial sensor to sense the physiological needs of the body. One sensor which can replace the atrial sensor is a pH sensor. During exercise, the blood pH decreases. Thus, by continuously sensing the blood pH the physiological needs and, thus, the required cardiac output can be substantially determined. Like the atrial sensor, the pH sensor continually transmits information back to the microprocessor contained within the pacemaker. Also, like the atrial sensor, the pH sensor is used along with the two power sensors. While the physiological needs of the body can be adequately sensed by the pH sensor other sensors may be employed along with the pH sensor to act as backups and to provide an even more accurate measurement of the physiological needs of the body. These sensors include a blood pressure sensor, a blood oxygen level sensor, and a blood carbon dioxide level sensor. One or any combination of the three sensors may be used along with the blood pH sensor.

While not absolutely necessary for the operation of the apparatus, an adaptor can be implanted subcutaneously or transcutaneously which would be connected to the flexible tubing connecting the reservoir to the artificial heart. This adapter would allow an external power source to be connected rapidly to the apparatus if the need were to arise.

The apparatus of this invention is particularly useful with a pressure actuated artificial heart and most particularly with the Jarvik-7 artificial heart. Basically, the Jarvik-7 heart comprises a right ventricle chamber and a left ventricle chamber. Both the right and left ventricle chambers have an inflow valve and an outflow valve for permitting the circulation of blood into and out of the chamber. In addition, each chamber contains a deformable diaphram which divides each chamber into a blood containing section and power fluid containing section.

The left and right ventricle chambers of the artificial heart fill with blood during the diastolic portion of the cardiac cycle. When the left and right ventricles are in this state, the rectus femoris muscle is in a relaxed state and thus the piston is in its extended position in the cylinder and the fluid is uncompressed. When the muscle is stimulated by an electrical signal from the pacemaker, it contracts against the cylinder thereby forcing the piston to move into the cylinder. Fluid within the cylinder is thus pressurized and caused to flow out of the cylinder through the flexible tubing toward the artficial heart. The fluid within the tubing adjacent the artificial heart enters both the left and right ventricle chambers and deforms the diaphragm in each chamber to create an artificial systole whereby the blood is expelled from both ventricle chambers through outflow valves.

After the appropriate amount of time, as determined from the information supplied by the sensors to the microprocessor, the pacemaker ends its transmission of the electrical signals through the stimulatory electrodes and the muscle relaxes. The piston-cylinder reservoir then returns to an uncompressed state thereby forming a partial vacuum in the cylinder. A spring may be disposed in the cylinder to aid this part of the cycle. The power fluid within the left and right ventricle chambers will then be drawn back toward the cylinder through the flexible tubing. Blood will then flow into the left and right ventricle chambers through the inflow valve so as to create an artifical diastole. Of course, the frequency, duration, and intensity of the artificial cardiac cycle will depend upon the physiological needs of the body as measured by the sensing electrodes.

A number of modifications to the preferred apparatus for powering a body implant device may be made. For example, the piston-cylinder reservoir may be attached to two muscles, rather than one muscle. Preferably, when two muscles are used the rectus femoris muscle and the gracilis muscle in the thigh are used. According to this embodiment, when the pacemaker transmits the appropriate electrical signals through the stimulatory electrodes, both muscles contract in unison and force the piston into the cylinder thereby pressurizing the fluid in the cylinder and the remainder of the system and causing it to flow into the artificial heart. Thus, the additional muscle adds power to the apparatus and acts as a backup should anything go wrong with either of the muscles. In another similar embodiment, the pacemaker is programmed to alternate stimulatory signals to both muscles so that the two muscles alternately contract. In this manner, the individual muscles can rest for a complete cardiac cycle, while the power output remains continuous.

Further modifications include employing two piston cylinder reservoirs instead of a single piston-cylinder reservoir. The advantage to this system is that a spasm of one muscle would not immobilize the other muscle which could thus continue to operate its own power cylinder. In this system, both muscles can be stimulated simultaneously so as to cause the contraction of both muscles simultaneously thereby causing the fluid within both reservoirs to flow to the artificial heart at the same time. Alternatively, the pacemaker could be programmed to cause the muscles to contract at various intervals which could result in a period of inactivity of one muscle and reservoir ranging from alternate cardiac cycles to extended periods.

In still a further embodiment, the piston-cylinder reservoir is replaced by a deformable balloon reservoir. The deformable balloon reservoir which is connected by flexible tubing to the artificial heart is preferably implanted in the axilla of the body between the third, fourth and fifth ribs and the pectoralis minor muscle which is stretched across the balloon and attached to the third, fourth and fifth ribs. Like the apparatus of the preferred embodiment, stimulatory electrodes from the pacemaker are woven through the pectoralis minor muscle. Electrical signals from the pacemaker cause the pectoralis minor muscle to contract thereby compressing the deformable balloon against the third, fourth and fifth ribs to pressurize the fluid in the balloon reservoir, and in the remainder of the system thereby causing it to flow toward the artificial heart. Thus, the operation of the device of this embodiment is very similar to the operation of the device disclosed in the preferred embodiment.

These and other modifications and advances of the apparatus for powering a body implant device will be more fully appreciated from the following detailed description and annexed drawings of the preferred embodiment thereof.

BRIEF DESCRIPTION OF THE DRAWINGS

In the drawings:

FIG. 7 is a view similar to FIG. 3 showing another embodiment; and

FIG. 8 is a view similar to FIG. 3 showing still another embodiment.

DESCRIPTION OF THE PREFERRED EMBODIMENTS

Figure 1:
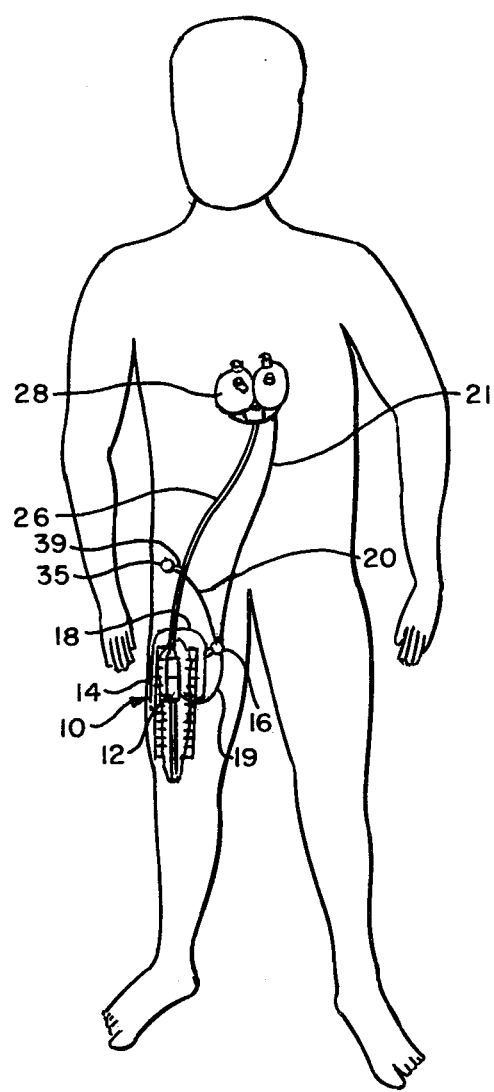
FIG. 1 is a diagrammatical view of the preferred apparatus for powering a body implant device implanted in the body according to the present invention.

Referring now to the drawings in detail and initially to FIG. 1, the preferred apparatus for powering a body implant device is generally designated by reference numeral 10. As defined herein, the term "body implant device" means a rhythmically operable pulsating device such as an artificial heart, a pressure actuated ventricular assist device or an artificial diaphram. The apparatus is particularly useful for powering an artificial heart and most particularly for powering the Jarvik-7 artificial heart. Thus, while the apparatus is useful for powering various body implant devices, it will be described herein with reference to the Jarvik-7 artificial heart. Of course, as technology improves on the Jarvik-7 artificial heart, the improved devices, assuming they are pressure actuated, may be employed herein without departing from the invention.

In FIG. 1, the apparatus 10 is diagrammatically illustrated as being implanted in the body with portions of the body unessential to this invention not shown. As shown, the principal components of the apparatus are a fluid containing piston-cylinder type reservoir 12 attached to a body muscle 14, a pacemaker 16 including stimulatory electrodes 18 implanted in the muscle 14 and sensors 19, 20, and 21 connected to the artificial heart and apparatus 10 for sensing the body's physiological needs and power output of body muscle 14, and tubing 26 for connecting the piston-cylinder reservoir 12 to a body implant device such as an artificial heart 28.

Figure 3:
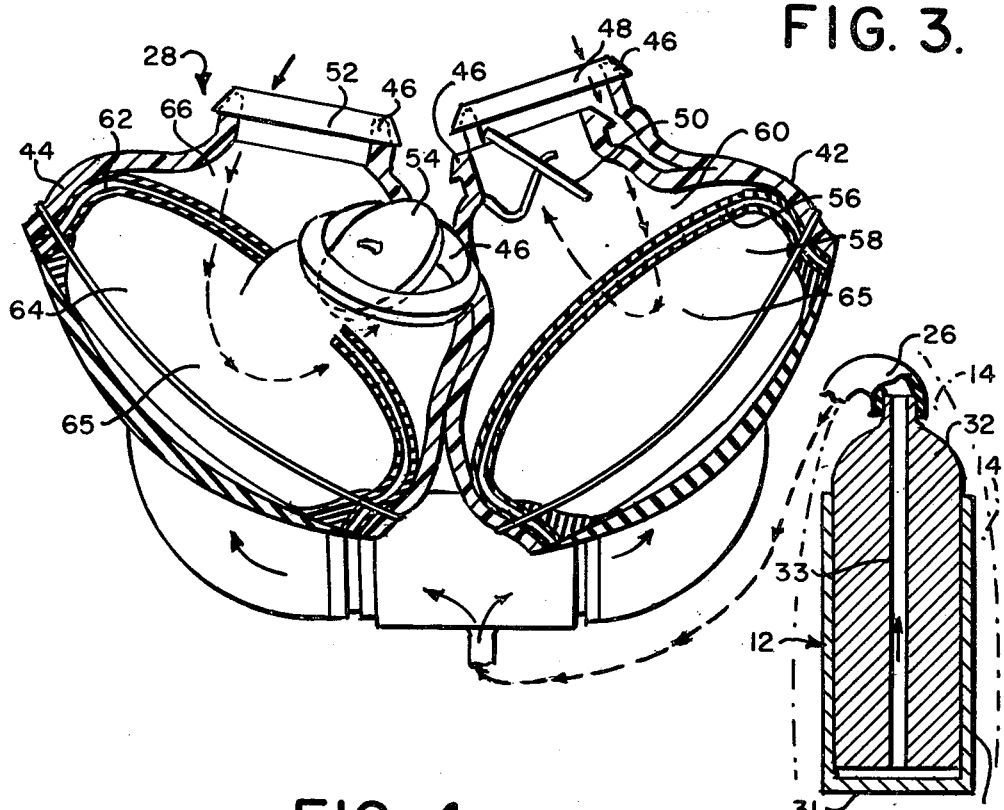
FIG. 3 is a diagrammatical view of the preferred apparatus of the preferred embodiment showing the apparatus and the artificial heart during the systolic portion of the cardiac cycle.
Figure 4:
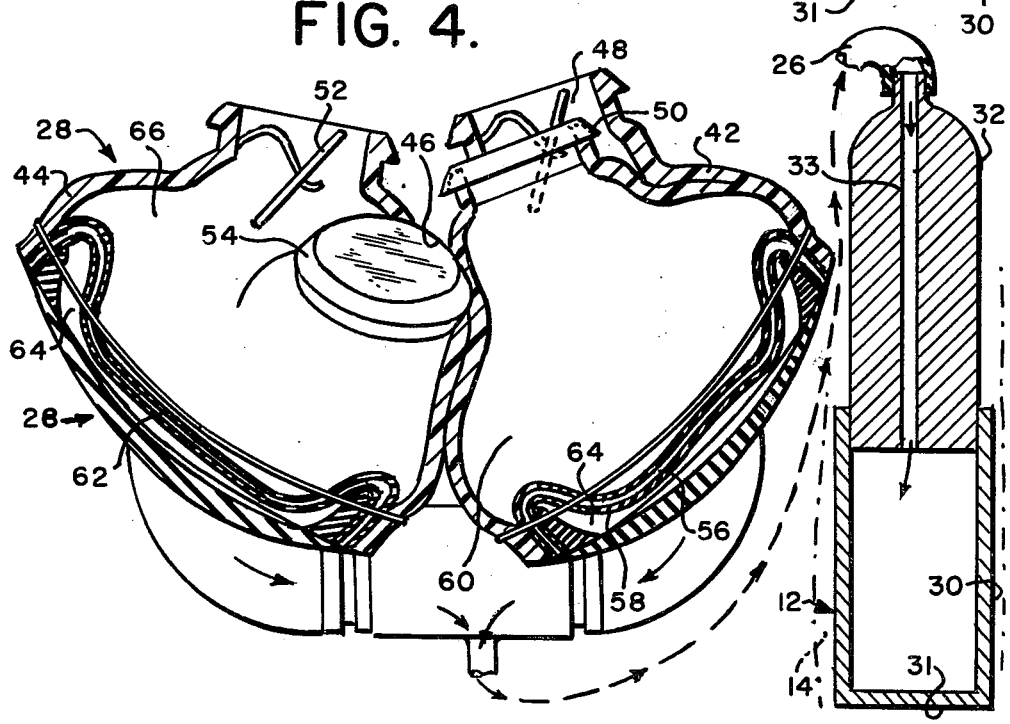
FIG. 4 is similar to FIG. 3 but showing the apparatus during the diastolic portion of the cardiac cycle.
Figure 5:
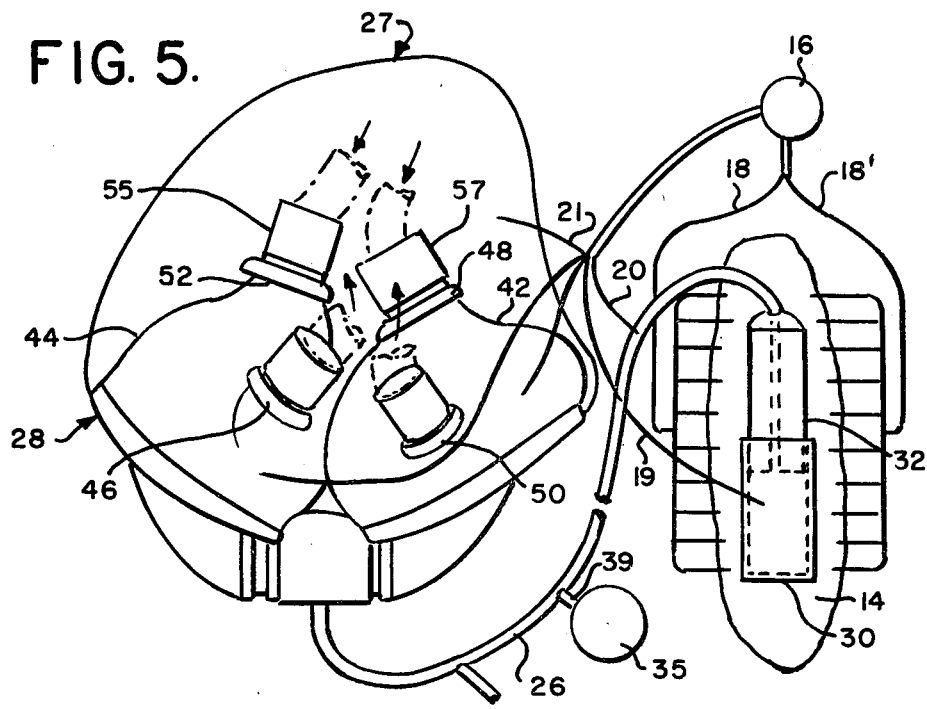
FIG. 5 is a diagrammatical view of the apparatus of the preferred embodiment, external of a human or animal body.

As best illustrated in FIGS. 3, 4 and 5, the piston-cylinder reservoir 12 comprises a cylinder 30 for containing a fluid and a piston 32 slidably disposed therein. While not absolutely necessary for the operation of the apparatus, a spring (not shown) may be connected between the end of the piston disposed within the cylinder and cylinder end wall 32. This spring will assist the piston in returning to a extended position after it is compressed into the cylinder 30. As shown, the piston 32 has an inlet-outlet opening 33 extending centrally through the piston along its entire length through which fluid may enter and exit the cylinder. As presently preferred, the cylinder 30 has an inner diameter of about 6 centimeters and a stroke length of about 7.5 centimeters. A piston-cylinder reservoir having such dimensions can expel about 200 ml. of fluid if the piston is completely compressed into the cylinder, as shown in FIG. 3. The reservoir 12 may be constructed from any type of bio-compatable material such as stainless steel, or bio-compatable plastics. It is presently preferred to construct the piston-cylinder reservoir 12 of stainless steel. A piston-cylinder reservoir meeting the above parameters is the Clippard DS-32-3 manufactured by Clippard Instrument Company, Cincinnati, Ohio.

Figure 2:
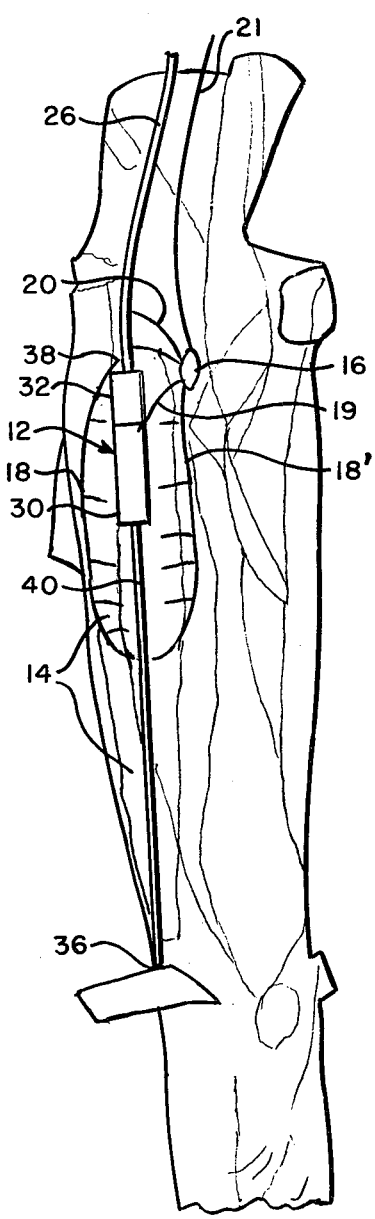
FIG. 2 is a fragmentary exploded view showing the piston-cylinder reservoir of the preferred apparatus implanted in the thigh.

As presently preferred, and as best shown in FIG. 2, the piston-cylinder reservoir 12 is implanted in the body in the thigh and is attached to the rectus femoris muscle 14. While the rectus femoris muscle is presently considered to be the most suitable muscle, other muscles in the thigh may be used. These muscles include the sartorius, gracilis, vastus lateralus, and the vastus intermedius. While the thigh is the presently preferred sight of implantation of reservoir 12, reservoir 12 may be implanted in other portions of the body. For example, the piston-cylinder reservoir may be implanted in the upper arm wherein the bicep muscle can be used as the attachment muscle.

Prior to implantation of piston-cylinder reservoir 12 in the thigh, the muscle is exposed and by normal surgical procedures the sensory and motor innervation of the muscle are sacrificed. The origin and insertion of the muscle are then severed and attached to the opposite ends of the piston-cylinder reservoir 12. As shown, the insertion 36 of the muscle (the portion normally attached to a mobile bone) is attached to an extension rod 40 which is directly connected to the cylinder portion 30 of the reservoir 12 and the origin 38 of the muscle (the portion normally attached to a more stable bone) is attached to the piston 32. The extension rod 40 is required since the rectis femoris is longer than the piston-cylinder reservoir 12. The muscle 14 can be attached to the piston-cylinder reservoir 12 in any suitable manner such as adhesively bonding the insertion and origin ends of the muscle to the piston-cylinder reservoir. However, it is presently preferred to suture the origin and insertion ends of the muscle to the piston-cylinder reservoir. Since the muscle remains in its normal location in the body after attachment to the reservoir 12 it receives normal nourishment from the vascular system.

In FIGS. 2, 4 and 5, the piston-cylinder reservoir is shown in an extended position. Contraction of the muscle forces the piston 32 into cylinder 30 (FIG. 3) thereby pressurizing the fluid contained within the cylinder and causing it to flow out of the cylinder through opening 33 to displace fluid in tubing 26 to thereby force fluid in the tubing into artificial heart 28. A more detailed esplanation of the complete operation of the apparatus will be described hereinafter. The tubing 26 which connects the piston-cylinder reservoir 12 to the artificial heart 28 is implanted subcutaneously and routed by normal surgical procedures between the thigh and the artificial heart which is implanted in place of the natural heart in the chest cavity. Any suitable flexible surgical tubing constructed from a bio-compatable plastic may be employed. The tubing presently preferred is Bentley "Implant Tested" pressure tubing, of polyvinyl chloride composition, produced by Bentley Labs., Irvine, Calif.

Prior to implantation of the piston-cylinder reservoir in the body it is filled with an actuating fluid. A skilled art worker will appreciate that a variety of different fluids may be employed. The fluid may be chosen from a wide range of pure substances and mixtures. Nitrogen is presently preferred; however, any suitable gas may be used. Moreover, while gases are preferably preferred, liquids and even gels may be substituted. Therefore, as used throughout, the term fluid contemplates any such suitable substance.

The cardiac pacemaker 16 is utilized to periodically stimulate the muscle 14 to cause it to contract. A programmable pacemaker containing a microprocessor is presently preferred. While the pacemaker may be implanted in any portion of the body it is preferably implanted near the reservoir 12 to facilitate easy connection of the stimulating electrodes 18 to the muscle. Thus, as shown in FIG. 2, the pacemaker 16 is implanted in a subcutaneous pouch in the thigh near the rectus femoris muscle. Its operation can be monitored using the appropriate external sensory devices well know in the art. Preferably, the external monitor would be connected to an alarm system. As best illustrated in FIG. 5, the pacemaker includes stimulatory electrodes 18 which are woven through the actuating muscle, her the rectus femoris muscle, and sensor electrodes 19, 20 and 21. The sensor electrodes include a pair of sensors 19 and 20 for sensing the power output of the muscle 14 and at least one sensor electrode 21 for sensing the physiological needs of the body.

If the atrial portion 27 of the natural heart remains after implantation of the artificial heart, a sensor electrode 21 is implanted in the atria to sense the frequency of the endogeniously controlled sinoatrial or atrioventricular node. The sinoatrial node, known as the SA node or pacemaker, is located in the right atrial wall inferior to the opening of the superior vena cava. The SA node initiates the cardiac cycle, and thereby sets the basic pace for the heart rate. Once an electrical pulse is initiated by the SA node, the impulse spreads out over both atria, causing them to contract and at the same time depolarizing the atrioventricular (AV) node. Thus, by sensing the frequency of the endogeniously controlled SA or AV node, the physiological needs of the body can be determined. The information obtained from the atrial sensor is continuously transmitted to a microprocessor (not shown) which is contained in the pacemaker 16.

In addition to sensing the body's physiological needs by means of atrial sensor 21, it is also necessary to continuously sense the power being generated by the rectus femoris muscle. The power produced by the muscle may be monitored by connecting sensor 19 to strain and position gauges mounted on the piston-cylinder reservoir 12. Such a sensor will monitor the tension exerted by the muscle on the reservoir when the muscle 14 is contracted. When using a piston-cylinder reservoir having a 6 cm diameter cylinder and a stroke length of 7.5 cm, as described above, the tension generated by the muscle, in order to fully displace the piston within the cylinder, will be from about 15 to about 20 lbs. Alternatively, the power of the muscle may be monitored by sensing the pressure exerted by the fluid after it is expelled from the reservoir. This may be done by placing a pressure sensor 20 in tubing 26. A fluid pressure of about 2.5 lbs./sq. in. to about 5.0 lbs./sq. in. is presently preferred and can be obtained using the preferred piston-cylinder reservoir 12 with a muscle exerting a tension of from about 12.5 to about 25 lbs. The pressure is sensed by a pressure sensing electrode 20 positioned within the tubing 26. It is presently preferred to employ both power sensors 19 and 20 along with the atrial sensor 22. If the muscle at any time becomes strained or tired, the reduced power of the muscle must be compensated for by increasing the intensity of the electrical signal transmitted by the pacemaker.

All the information obtained by the sensors 19, 20 and 21 is continually transmitted to the microprocessor in the pacemaker. Any suitable microprocessor known in the art may be employed. Based on the information transmitted to the microprocessor by the electrodes, the appropriate electrical signals are transmitted by the pacemaker through the stimulatory electrode 18 to stimulate the rectus femoris muscle, resulting in the generation of the appropriate fluid pressure in the reservoir 12 and, thus, the appropriate cardiac output. The intensity, frequency and duration of the stimulation will vary depending upon the body's physiological needs, which will be related to the power being generated by the muscle, and thus to cardiac output.

If, however, the atrial portion of the natural heart does not remain after the implantation of the artificial heart one or more other sensor may be used in place of the atrial sensor to determine the physiological needs of the body. One sensor which can replace the atrial sensor is a pH sensor (not shown). Preferably, the pH sensor comprises an iridium oxide electrode which is placed in the pulmonary artery to sense the blood pH. During exercise, the blood pH decreases and the ventricular rate increases. Thus, by continually sensing the blood pH the physiological needs and necessary cardiac output can be substantially determined. The pH electrode continuously transmits blood pH information to the microprocessor in the pacemaker. Like the atrial sensor, the pH sensor is used along with power sensors 19 and 20. While the physiological needs of the body can be adequately sensed by the pH sensor, other sensors may be employed along with the pH sensor to act as backups and to provide an even more accurate measurement of the physiological needs of the body. These sensors include a blood pressure sensor, a blood oxygen level sensor and a blood carbon dioxide level sensor. If the blood pressure sensor is used, the sensing electrode is preferably placed in the aorta, although some other major artery may be employed. If blood oxygen level sensor is used, the sensing electrode is positioned preferably in the pulmonary artery, although some other artery may be used. Finally, if the carbon dioxide sensor is employed, the sensing electrode is disposed preferably in the pulmonary artery, although another suitable artery may be employed. One or any the three additional sensors may be used along with the blood pH sensor. Information obtained by the additional sensors is, like that derived from the previously discussed sensors, transmitted to the microprocessor in the pacemaker.

While not absolutely necessary for the operation of the apparatus 10, an adaptor (not shown) can be implanted subcutaneously or transcutaneously which would be connected to tubing 26. This would allow an external power source to be connected rapidly to the apparatus 10 if the need were to arise.

Also, while not absolutely necessary for the operation of the apparatus, it is presently preferred to employ a damping device for damping the long term pressure changes (several seconds or longer) which could be caused by muscle spasms. As best shown in FIG. 5, the damping device 35 preferably comprises an elastic reservoir connected by a small ostium to the main tubing 26. If a pressure change of long duration were to occur in the apparatus 10 (as from a spasm of the power muscle 14) a sufficient quantity of fluid would flow into or out of the elastic reservoir to alter the pressure in the main system, thus acting to return the pressure to near normal. During the transient pressure pulses, such as those generated by a normally contracting power muscle, insufficient fluid will flow into or out of the elastic reservoir to significantly alter the pressure. While the damping system described above is presently preferred because of its simplicity, other suitable damping systems for maintaining a constant pressure over a wide range of volume may be employed, especially one manufactured by Metal Bellows Corp., Sharon, Mass.

As described previously, the apparatus of this invention is particularly useful with a pressure actuated artificial heart and, presently, most particularly with the Jarvik-7 artificial heart. As best illustrated in FIGS. 3, 4 and 5 the Jarvik-7 heart comprises a right ventricle chamber 42 and a left ventricle chamber 44. The right and left ventricle chambers 42 and 44, respectively, are constructed of polyurethane supported on an aluminum base. Polycarbonate rings 46 support tilting disc valves 48, 50 52 and 54. As shown, the right ventricle chamber 42 has an in-flow valve 48 and an out-flow valve 50. The left ventricle 44 similarly has an in-flow valve 52 and an out-flow valve 54. The dacron patches 55 and 57 depicted on the inflow valves 52 and 50 of the heart in FIG. 5 provide the means of coupling the artificial heart to the circulatory system of the patient in which it is implanted. The right ventricle has a double-walled deformable diaphram 56 which divides the ventricle chamber into a fluid containing portion 58 and blood containing portion 60. Similarly, the left ventricle has a double-walled deformable diaphram 62 which divides the left ventricle into a fluid containing portion 64 and blood containing portion 66.

The artificial heart illustrated in FIG. 4 is shown during the diastole portion of the cardiac cycle when the blood enters the ventricles. As shown, in-flow valves 48 and 52 are open to permit blood to flow into the right and left ventricle chambers while out-flo vales 50 and 54 are in a closed position so as to prevent flood from blowing back into the right and left ventricle chambers. As shown in FIG. 4, blood has entered the right and left ventricle chambers and compressed the deformable diaphrams 56 and 62 against the wall of the right and left chambers, respectively. In FIG. 3, the artificial heart is illustrated as it appears during the stystole portion of the cardiac cycle when the blood is expelled from the ventricles. As shown, the in-flow valves 48 and 52 are in a closed position so as to prevent blood from flowing back into the atria, whereas valves 50 and 54 are in an open position so as to allow blood to flow out of the ventricles. Also, the diaphrams 56 and 62 within the right and left ventricle chambers are shown as being deformed into the chambers by fluid 65 which is contained in the fluid containing portions 58 and 64 of the right and left ventricle chambers, respectively.

The operation of the apparatus during a single cardiac cycle comprising of a diastol and systole will now be described with reference to FIGS. 3 and 4. FIG. 4 illustrates the apparatus 10 during diastole. The muscle 14 is in a relaxed state and thus cylinder 12 is extended. When muscle 14 stimulated by an electrical signal from the pacemaker, it contracts against the cylinder 12 thereby forcing piston 32 to enter the fluid containing cylinder 30. The fluid within the cylinder 12 is thus pressurized and caused to flow out of the cylinder through tubing 26 to force fluid in the system to the artificial heart 28. The pressurized fluid enters both the left and right ventricle chambers 42 and 44 and deforms the diaphrams 56 and 62 toward the position shown in FIG. 3 to create an artificial systole whereby the blood is expelled from the left and right ventricle chambers through out-flow valves 50 and 54. After the appropriate amount of time, as determined from the information supplied by the sensors to the microprocessor within the pacemaker, the pacemaker ends its transmission of the electrical signal through the stimulatory electrodes and the muscle 14 will relax. The piston-cylinder reservoir 12 will then return to the retracted position shown in FIG. 4 thereby causing a partial vacuum in the cylinder. The fluid within the system will then be drawn back toward the cylinder through tubing 26 to thereby remove pressure from the deformable diaphragms 56 and 62. This will cause blood to flow back into the left and right ventricle chambers through in-flow valves 48 and 52 so as to create an artificial diastole (FIG. 4). The frequency, duration, and intensity of the artificial cardiac cycle will depend upon the physiological needs of the body as measured by the sensing electrodes.

Skilled art workers will recognize that a number of changes and modifications may be made to apparatus 10 for powering a body implant device. Like components have the same reference numerals as in the preferred embodiment. With reference to FIG. 7, piston-cylinder reservoir 12 is shown as being attached to two muscles 14 and 72, rather than to one muscle as shown in FIG. 2. As illustrated, the piston-cylinder reservoir 12 is attached to both the rectus femoris muscle 14 and the gracilis muscle 72 in the thigh. Other muscles in the thigh may, however, be used instead of the rectus femoris and gracilis. Alternatively, the reservoir 12 may be implanted in another portion of the body and attached to the two muscles at the site of implantation. As shown, stimulatory electrodes 18 from pacemaker 16 are woven through both muscles. The operation of apparatus 10 having a piston-cylinder reservoir 12 attached to the two muscles as described above is similar to the operation of the preferred apparatus. Thus, when pacemaker 16 transmits the appropriate electrical signals through stimulatory electrodes 18, the muscles 14 and 72 contract in unison and compress the piston 32 into cylinder 30 thereby pressurizing the fluid in the cylinder and causing it to flow to the artificial heart through tubing 26. In this embodiment, the additional muscle 72 adds power to the apparatus and acts as a backup should be anything go wrong with either muscle 14 or 72, such as a spasm.

In another similar embodiment, the pacemaker is programmed to alternate stimulatory electrical signals to muscles 14 and 72 so that the two muscles alternatively contract. In this manner, the individual muscle can rest for a complete cardiac cycle, while the power output remains continuous.

A still further embodiment is illustrated in FIG. 8. As shown in FIG. 8, two piston-cylinder reservoirs 12 and 76 are employed instead of a single piston-cylinder reservoir. Each of the reservoirs 12 and 76 is attached to its own muscle, as for example and as presently preferred muscles 14 and 72, respectively, in the thigh. While any two muscles may be employed, it is presently preferred to use the rectus femoris and gracilis muscles of the high in this two-muscle system. As shown, tubing 78 connected to reservoir 76 and tubing 80 connected to reservoir 12 join to form one main connecting tubing 82 which connects the reservoirs 12 and 76 to the artificial heart. As shown, stimulatory electrodes 18 from pacemaker 16 are woven into both muscles 14 and 72. In this embodiment, both muscles are stimulated in unison so as to cause the contraction of both muscles simultaneously. As a result fluid is expelled from both reservoirs simultaneously and caused to flow from the reservoirs to the artificial heart. In an alternative embodiment, the pacemaker 18 is programmed to cause the muscles to contract at various intervals which could result in a period of inactivity of one muscle and reservoir ranging from alternate cardiac cycles to alternate extended periods. In this system, a spasm of one muscle would not immobilize the other muscle, which could thus continue operating its own power cylinder. While this embodiment has been described with reference to two power cylinders attached to separate muscles, it is obvious that more than two reservoirs can be employed, each of which is attached to its own power muscle.

Figure 6:
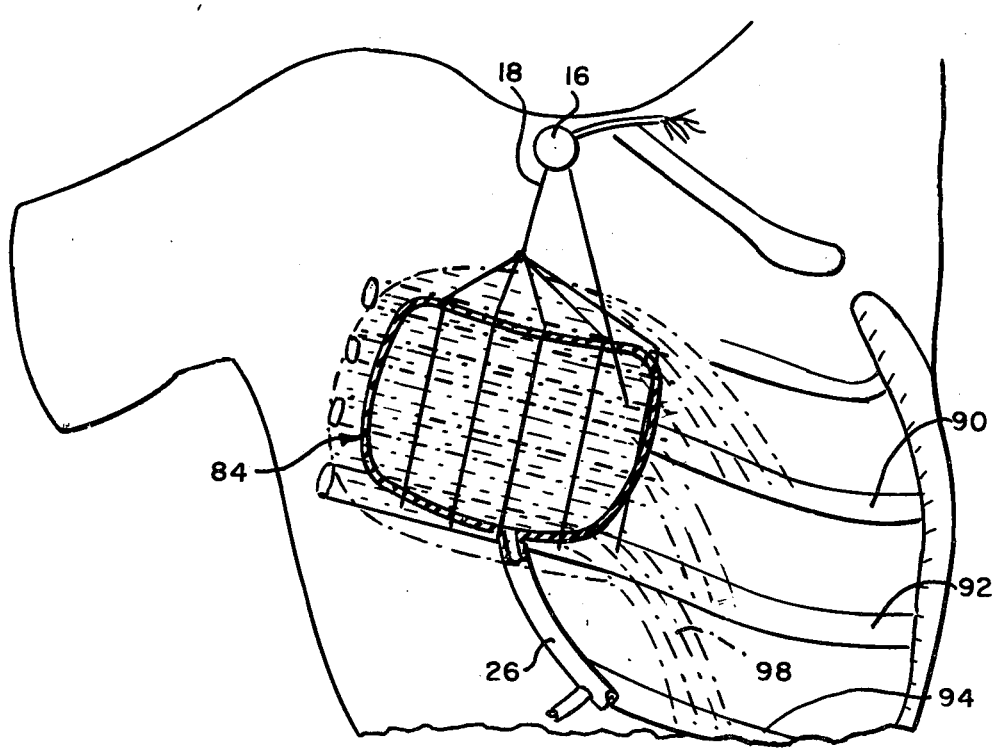
FIG. 6 is a fragmentary exploded view showing the balloon reservoir of another embodiment positioned in the axillary region of the body.

A still further embodiment is illustrated in FIG. 6. In this embodiment, a deformable balloon 84 is used instead of the piston-cylinder reservoir 12. While the deformable balloon reservoir 84 can be constructed from any suitable material, it is presently preferred to be constructed from a bio-compatible plastic. Suitable plastics include; Biomer, a polyether manufactured by Ethicon, Tecoflex, a linear segmented aliphatic polyurethane, manufactured by Thermo Electron Co.; and polyolefin rubber compositions. As shown, the balloon reservoir 84 is implanted in the axilla region of the body between the second, third, fourth and fifth ribs 90, 92, and 94, respectively, and the pectoralis minor muscle 98 which is pulled across the top surface of the balloon 84 and attached to the third, fourth and fifth ribs at the posterior axillary line. While the axilla region is presently considered to be the most desirable implantation site for the balloon reservoir 84, it may be implanted in other suitable regions of the body.

Prior to the implantation of the balloon reservoir 84 in the axilla, the sensory and motor innervation of the pectoralis minor muscle is sacrificed by normal surgical procedures. Insertion of the pectoralis minor muscle is then severed from the coracoid process of the scapula. The balloon reservoir 84 is then implanted in the axilla adjacent the third, fourth and fifth ribs and pectoralis minor muscle is pulled over the balloon reservoir 84 and attached to the third, fourth and fifth ribs at the axillary line, as shown in FIG. 6. The other principal components of the apparatus 10 are the same as those described with reference to FIGS. 2, 3 and 4. Thus, a pacemaker 16 is implanted by normal surgical procedures in a subcutaneous pouch near the balloon reservoir 84. As shown, stimulatory electrodes 18 are woven through the pectoralis minor muscle. The sensor electrodes are connected in the same manner as described with reference to FIGS. 2 and 5. As shown, flexible tubing 26 connects the balloon reservoir 84 to the artificial heart.

The operation of the apparatus with the balloon reservoir is similar to the operation of the apparatus described in FIGS. 3 and 4 utilizing a piston-cylinder reservoir 12. Thus, when the pectoralis minor muscle receives electrical signals through the stimulatory electrodes 18 from the pacemaker 16, it contracts. Contraction of the pectoralis minor muscles compresses the balloon against the underlying third, fourth and fifth ribs thereby pressurizing the fluid in the balloon reservoir and causing it to flow through tubing 26 to the artificial heart.

In yet another embodiment, the stimulatory electrode stimulates the motor nerve serving the power muscle or muscles, instead of stimulating the muscle directly. Power requirements in this embodiment would be significantly reduced. Obviously, in this embodiment, the motor nerve to the muscle would be preseved, while the sensory innervation would be sacrificed by micro surgery. In this embodiment, a stimulatory electrode located in the spinal cord, or cerebral cortex, or encasing a portion of the peripheral nerve would be employed.

Since these and other changes and modifications are within the scope of the present invention, the above description should be construed as illustrative and not in the limiting sense, the scope of the invention being defined by the following claims.

I claim:

1. A device comprising in combination a body implant device and an apparatus for powering said body implant device; said device comprising a reservoir; said reservoir being implantable in the body adjacent to at least one muscle; a fluid disposed within said reservoir; a pressure actuated body implant device; a conduit connecting said reservoir to said body implant device and providing a fluid connection between said reservoir and body implant device; means for periodically stimulating said at least one body muscle from a relaxed state to a contracted state for periodically contracting said at least one body muscle against said reservoir to pressurize said fluid to cause it to flow from said reservoir toward said body implant device; said body implant device including means responsive to said pressurized fluid for powering said body implant device; upon relaxation of said at least one muscle said reservoir returning to its original unpressurized state, thereby creating a vacuum so as to cause the return of said fluid thereto.

2. The device of claim 1, wherein said reservoir is a piston-cylinder reservoir comprising a piston slidably disposed within a cylinder.

3. The device of claim 2, wherein said means responsive to said pressurized fluid comprises a means for expelling blood from said body implant device.

4. The device of claim 3, wherein said body implant device comprises two chambers and said means for expelling blood from said body implant device comprises two deformable diaphrams, one disposed in each of said chambers of said body implant device.

5. The device of claim 4, wherein each of said deformable diaphrams divides each of said chambers of said body implant body implant device into a fluid containing section and a blood containing section, whereby when said fluid flows into said body implant device it enters said fluid containing section of each of said chambers and deforms each of said deformable diaphrams, thereby expelling blood from each of said blood containing sections of said chambers.

6. The device of claim 2, wherein said piston-cylinder reservoir is attached to two body muscles.

7. The apparatus of claim 3, wherein said means for stimulating said muscle comprises a pacemaker having stimulatory electrodes for connection to said body muscle.

8. The device of claim 7, wherein said pacemaker includes at least one sensor electrode for sensing the physiological needs of the body; said pacemaker including a microprocessor for receiving information from said at least one sensor, said microprocessor being capable of translating said information and instructing said pacemaker based on said information to transmit the appropriate electrical signals through said stimulatory electrodes to said body muscle.

9. The apparatus of claim 8, wherein said pacemaker includes an atrial sensor connectable to the atrial portion of the natural heart for sensing the frequency of the endogenously controlled sinoatrial or atrioventricular node; a tension sensor connectable to said reservoir for sensing the tension generated by at least one body muscle on said reservoir; and a pressure sensor connectable to said conduit for sensing the pressure exerted by the fluid in said conduit.

10. The apparatus of claim 8, wherein said pacemaker includes a pH sensor for sensing the pH of the blood; a tension sensor connectable to said reservoir for sensing the tension exerted by said at least one body muscle; and a pressure sensor connectable to said conduit for sensing the pressure exerted by the fluid in said conduit.

11. The apparatus of claim 10, wherein said pH sensor is connectable to the aorta.

12. The apparatus of claim 10, wherein said pacemaker additionally includes blood pressure sensor for sensing blood pressure.

13. The apparatus of claim 12, wherein said blood pressure sensor is connectable to the aorta.

14. The apparatus of claim 10, wherein said pacemaker additionally includes an oxygen sensor connectable to the pulmonary artery of the heart for sensing the oxygen content of the blood.

15. The apparatus of claim 14, wherein said oxygen sensor is connectable to the pulmonary artery.

16. The apparatus of claim 10, wherein said pacemaker additionally includes a carbon dioxide sensor connectable to the pulmonary artery of the heart for sensing the carbon dioxide content of the blood.

17. The device of claim 16, wherein said carbon dioxide sensor is connectable to the pulmonary artery.

18. The device of claim 1, wherein said reservoir is a deformable balloon.

19. The device of claim 18, wherein said deformable balloon is implantable in the axilla region of the body between the ribs and the pectoralis minor muscle.

20. The device of claim 19, wherein said deformable balloon is constructed from a bio-compatible plastic.

* * * * *